Figure 1:
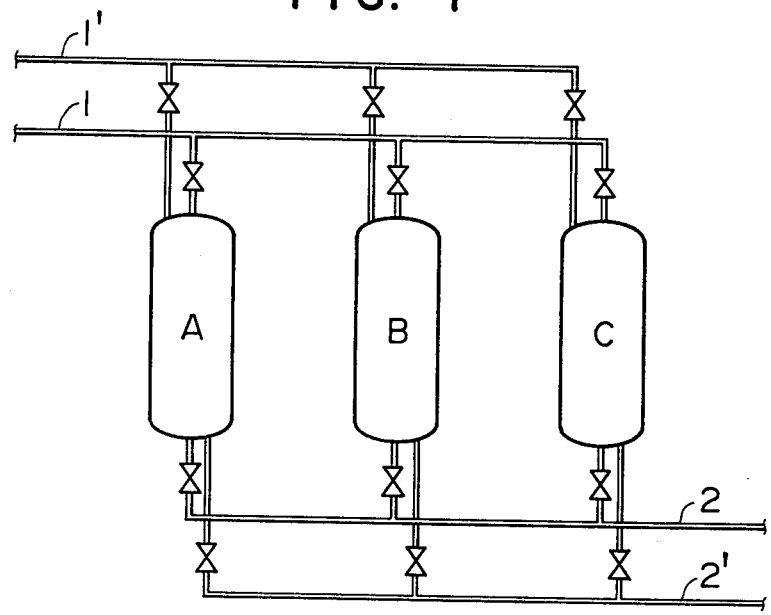

United States Patent [19]

Miyake et al.

[11] 4,285,811
[45] Aug. 25, 1981

[54] PURIFICATION OF FORMALDEHYDE BY SEPARATION

[75] Inventors: Tetsuya Miyake, Tokyo; Kunihiko Takeda, Yokohama; Naoki Miyata, Kawasaki; Tatsushi Saeki, Yokohama; Maomi Seko, Tokyo, all of Japan

[73] Assignee: Asahi Kasei Kogyo Kabushiki Kaisha, Osaka, Japan

[21] Appl. No.: 7,527

[22] Filed: Jan. 29, 1979

Related U.S. Application Data

[62] Division of Ser. No. 760,218, Jan. 17, 1977, Pat. No. 4,137,054.

[30] Foreign Application Priority Data

Jan. 22, 1976 [JP] Japan .................................. 51/5447

[51] Int. Cl.³ ............................................ B01D 15/00
[52] U.S. Cl. ................................ 568/422; 210/673; 210/677; 568/493
[58] Field of Search ................... 55/25, 26, 33, 62, 68, 55/75; 210/24, 38 R, 32, 34

[56] References Cited

U.S. PATENT DOCUMENTS

| 2,882,243 | 4/1959 | Milton | 55/75 X |
|---|---|---|---|
| 2,882,244 | 4/1959 | Milton | 55/75 X |
| 3,118,747 | 1/1964 | Codignola et al. | 55/33 |
| 3,176,444 | 4/1965 | Kiyonaga | 55/75 X |
| 3,186,144 | 6/1965 | Dow | 55/33 X |
| 3,493,618 | 2/1970 | Fuhrmann | 210/24 X |
| 3,597,169 | 8/1971 | Savage | 210/24 X |
| 3,636,679 | 1/1972 | Batta | 55/26 |
| 3,658,696 | 4/1972 | Shively et al. | 55/75 X |
| 3,998,901 | 12/1976 | Neuzil et al. | 210/24 X |
| 4,025,321 | 5/1977 | Anderson et al. | 55/33 |

*Primary Examiner*—Robert H. Spitzer
*Attorney, Agent, or Firm*—Sprung, Felfe, Horn, Lynch & Kramer

[57] ABSTRACT

A mixture containing formaldehyde and water is separated effectively by contacting with adsorbents of specific type A zeolites containing exchanged cations of the elements from Group IA (4) to (6) or Group IIA (6) or mixture thereof of the Periodic Table of Elements.

17 Claims, 2 Drawing Figures

PURIFICATION OF FORMALDEHYDE BY SEPARATION

This is a division, of application Ser. No. 760,218 filed Jan. 17, 1977, now U.S. Pat. No. 4,137,054.

This invention relates to purification by separation of formaldehyde. More particularly, this invention relates to a process for gas-phase separation of formaldehyde from water by adsorption separation, using as the adsorbents specific type A synthetic zeolites wherein the cations are composed principally of ions of the Group IA (4) to (6), IIA (6) or mixed ions thereof.

Formaldehyde is one of the important starting materials in commercial chemical industry. Typical commercial synthesis of formaldehyde is known as air-excess process, methanol-excess process, etc. In these processes, methanol is used as the principal starting material to give products consisting mainly of formaldehyde, methanol and water.

On the other hand, demand for a high purity formaldehyde has been increased as the progress of the chemical industries wherein a high purity formaldehyde is used as the starting material, for example, manufactures of polyacetal which is the polymer of formaldehyde. Accordingly, there have been made various investigations over the art for separation between formaldehyde and water or between formaldehyde and alcohol. Thus, there have been proposed such separation purification processes as distillation process, extraction process, hemi-acetal process, freezing process or combination thereof. However, each of these processes involves many problems to be solved in accomplishing purification by separation of formaldehyde in a high purity with high efficiency. First of the difficulties is that formaldehyde forms a complex with water and there exists an equilibrium relation therebetween. Secondly, formaldehyde is chemically very unstable to undergo readily polymerization or decomposition. Thirdly, formaldehyde industries, e.g. polyacetal industry, in which a high purity formaldehyde is required, have severe demands for formaldehyde with as high a purity as possible which is also required to be constant. For this purpose, for example, when a high purity formaldehyde is obtained from a mixture containing equal amounts of formaldehyde and water, separation is first effected by means of, for example, distillation, followed by formation of hemi-acetal adducts with alcohols to further perform decomposition and separation, and thereafter purity is further enhanced by means of freezing method, etc. Such a procedure is not only poor in efficiency but also has losses and other troubles in the steps of hemi-acetal formation and freezing. No further improvement is almost impossible to be expected of such a process.

The object of the present invention is to provide a commercially applicable improved process for production of a high purity formaldehyde.

According to the present invention, there is provided a process for purification of formaldehyde by separation, which comprises contacting a mixture of formaldehyde and water with adsorbents selected from the group consisting of type A synthetic zeolites wherein the cations contains at least one of the Group IA (4) to (6) and Group IIA (6) of the Periodic Table of Elements to separate into a stream enriched in formaldehyde and that enriched in water.

The type A structured synthetic zeolites herein contemplated refer to crystalline aluminosilicates belonging to the third group in the classification of crystals. They can be represented in terms of the mole oxides for the sodium form as represented by the formula: $Na_2O.Al_2O_3.2SiO_2.4.5H_2O$. They have the parameters as follows: density, 1.99 g/cc; unit cell volume, 1870 $Å^3$; unit cell constants $a=12.32$ Å (pseudo cell) and $a=24.64$ Å (true cell); void volume, 0.47 cc/cc; cage types, $\alpha$ and $\beta$; aperture in a non-hydrated state, 4.2 Å; kinetic aperture, 3.9 Å and 3.6 Å. They have the X-ray diffraction spectrum as shown in the following Table. The above characteristic values are shown for the sodium form of the type A zeolites which are generally synthesized in the sodium form. There are changes in these values when cations are exchanged.

| hkl | d(A) | I |
| --- | --- | --- |
| 100 | 12.29 | 100 |
| 110 | 8.71 | 69 |
| 111 | 7.11 | 35 |
| 210 | 5.51 | 25 |
| 211 | 5.03 | 2 |
| 220 | 4.36 | 6 |
| 221 | 4.11 | 36 |
| 311 | 3.71 | 53 |
| 320 | 3.417 | 16 |
| 321 | 3.293 | 47 |
| 410 | 2.987 | 55 |
| 411 | 2.904 | 9 |
| 420 | 2.754 | 12 |
| 421 | 2.688 | 4 |
| 332 | 2.626 | 22 |
| 422 | 2.515 | 5 |
| 430 | 2.464 | 4 |
| 511 | 2.371 | 3 |
| 520 | 2.289 | 1 |
| 521 | 2.249 | 3 |
| 440 | 2.177 | 7 |
| 441 | 2.144 | 10 |
| 530 | 2.113 | 3 |
| 531 | 2.183 | 4 |
| 600 | 2.053 | 9 |

Exchange of cations in the type A synthetic zeolites can be accomplished by a known method. For example, the type A synthetic zeolite in the sodium form is contacted with an aqueous solution of water-soluble potassium salt or barium salt or a mixture of potassium salt and barium salt. As potassium salts, there can usually be employed chlorides, nitrates, sulfates, carbonates, thiocyanates, etc. As barium salts, chlorides are generally used. Nor easy exchange of cations, it is desired to employ cation salts to be placed in excess of the equivalent amount and also to perform ion exchange under heating. Furthermore, a sufficient exchange time is required, since there occurs change in micro-structure of the crystal by cation exchange.

The exchange ratio of cations is important in the present invention. The ratio of the specific cations of the present invention, namely potassium, cesium, rubidium and/or barium is generally in the range from 60 to 100 wt.%, preferably from 80 to 100 wt.%, the balance being other cations, based on the total exchangeable cations. Presence of other cations outside the above range is not desirable since they may cause decomposition or polymerization of formaldehyde. They include, in addition to sodium and hydrogen, Group IA and Group IIA elements such as calcium, lithium, magnesium or strontium; the first transition elements such as titanium, vanadium, chromium, molybdenum, iron, cobalt nickel and copper; the second transition elements, most of which have difficultly soluble or easily decomposable salts, such as zirconium, hafnium, niobium, tantalum, molybdenum, tungsten, technetium, rhenium, ruthenium, osmium, iridium, palladium, platinum, gold and silver; lanthanides such as lanthanum and cerium; actinides such as uranium; and other elements such as zinc, cadmium, mercury, tin and lead. The effect of the present invention cannot be changed greatly by admixture with other cations in an amount with the above specified range. Desirably, however, the exchangeable cations in the type A synthetic zeolite are exchanged with the specific cations of the present invention as much as possible. In connection with ionic radius, cesium and rubidium can only partly exchange the cations, namely 45% in case of cesium and about 68% in case of rubidium, and therefore the remainder of the cations is desired to be replaced by potassium. Furthermore, while barium can easily be exchanged to 100%, the remainder of the cations, if any, is desired to be exchanged by potassium.

Among the various ions within the scope of the present invention, potassium and barium ions are preferred. According to a preferred embodiment of the present invention, the composition of exchangeable cations of the type A synthetic zeolite used as adsorbent comprises 80% or more, more preferably 90% or more, of potassium ions or barium ions. According to a more preferred embodiment, said composition comprises 80% or more, more preferably 90% or more, of potassium and barium ions.

The type A synthetic zeolites which are exchanged with desirable cations as mentioned above are subjected to drying such as vacuum drying, freeze drying and activation by means of heating in an electric furnace before they are provided for use. The ratio of constituting elements and the exchange ratio of the adsorbent can be analyzed by elemental analyzer and the crystalline structure by X-ray diffraction spectrometer.

Judging from the X-ray diffraction table and separation experiment, the kinetic aperture of ion-exchanged zeolite in this invention seems to be 2.9 Å or less.

While the above type A synthetic zeolite can be used without no particular treatment, it has further been found that a very stable separation operation is possible under conditions which can widely be selected when the type A synthetic zeolite of the present invention is subjected to a specific treatment before being put to use. Thus, the present invention also discloses a process wherein the type A synthetic zeolites having cations composed substantially of Group IA, from fourth to sixth period, or Group IIA, sixth period, or mixture thereof are subjected to treatment by contacting with formaldehyde, ammonia, amines, urea compounds, or phosphoric acid compounds before being provided for use.

When the type A synthetic zeolite subjected to above pre-treatment is used as the adsorbent, recovery of formaldehyde is increased greatly because by-products such as methyl formate are suppressed to be formed and the purity of formaldehyde can also thereby be improved.

The treatment of the type A synthetic zeolite of the present invention with formaldehyde or ammonia may generally be conducted in gaseous or liquid phase. In case of treatment with formaldehyde, it is desired to treat the zeolite at a temperature in the range from 120° C. to 200° C. The treatment time is varied depending on the requirements in separation but can easily be determined experimentally. The treatment with amines or phosphoric acid compounds is recommended to be conducted in liquid phase, particularly in aqueous, alcoholic, acetone or dioxane solution.

The amines herein contemplated refer to alkyl amines such as methyl amine, trimethyl amine, diethyl amine, ethyl amine, butyl amine, benzyl amine, hexamethylene diamine, tetraethylene pentamine, etc.; alkanol amines such as ethanolamine, triethanolamine, etc.; and pyridines such as pyridine, lutidine, etc. It is noted that not only amines with comparatively small molecular weight but also alkyl amines having many carbon atoms with larger molecular size can be used.

The phosphoric acid compounds, which are preferred treating agents in the present invention, may include phosphoric acid, potassium primary phosphate, potassium secondary phosphate, potassium phosphate, and so on. Among these, phosphoric acid is most preferred. It is entirely unexpected that the type A synthetic zeolite, which is known to be dissolved in acids, is improved in stabilization of the adsorbent by treatment with phosphoric acid.

The treatment with phosphoric acid or a phosphate can be conducted under conditions suitably determined by experiments. For example, favorable results are obtained when the cation exchanged type A zeolite is treated with an aqueous or organic solvent solution with a concentration of phosphoric acid or phosphate of from 0.002 to 1.0 mol/liter in an amount corresponding to 0.1% to 20% by weight of phosphoric acid or phosphate based on the weight of the zeolite to be treated. In some cases, further improved results can be obtained by removing the excessive phosphoric acid or phosphate on the surface or in the interstitial voids of the zeolites by washing with water or an organic solvent.

According to the present invention, it has also been found that when the type A synthetic zeolite having the cations in the form of hydrogen ion are exchanged with ions of elements from the Group IA, from the fourth to sixth period, or of the Group IIA, the sixth period, or mixture thereof, the resulting zeolites can be used desirably as adsorbents to give better results. Since the type A zeolite has a ratio of silica to alumina of 1.0, it is poorly resistant to acids. Therefore, conversion into the hydrogen form by sufficient contact with strong acids such as hydrochloric acid or sulfuric acid is not advantageous. Accordingly, it is recommendable that the zeolite is first exchanged with ammonium ions and then subjected to treatment at a high temperature in the presence or absence of steam thereby to remove ammonia. The thus prepared zeolite with the hydrogen form can then be exchanged with ions within the scope of the present invention according to the process as described above. The zeolite prepared according to this method is also preferably subjected to pre-treatment with formaldehyde, ammonia, amines or phosphoric acid compounds according to the procedures as described above, before being provided for use as adsorbents. In this embodiment, phosphoric acid is found to be the most preferable treating agent.

In practicing the process of this invention, a mixture of formaldehyde and water is fed to separation apparatus containing the adsorbents as described above. Formaldehyde can be stable in liquid state when it coexists with other substances such as water or alcohol. However, when a high purity formaldehyde is formed at some part of the separation apparatus, formaldehyde present in liquid phase at said part may undergo polymerization thereby to cause irreversible changes. This phenomenon cannot be avoided even by use of the adsorbent of the present invention, since it occurs in liquid with no relevance with the adsorbent. This is why the separation is advantageously carried out in gas phase under which there is wide range of stable operating conditions. However, it is also possible to separate in liquid phase using suitable diluents which can stabilize formaldehyde.

For carrying out stable separation by adsorption in gas phase of formaldehyde, operation is conducted at a temperature in the range from 20° to 250° C., preferably from 120° to 200° C. under the partial pressure of formaldehyde in the range from 10 to 3100 mmHg, preferably from 500 to 1600 mmHg. The above ranges are experimentally determined and, under these conditions either formaldehyde copresent with water, alcohol and adsorbent or a high purity formaldehyde copresent with adsorbent is stable, whereby purification by separation can be performed sufficiently on a commercial scale.

The present process can effectively be applied for separation of unseparated crude formaldehyde mixture containing various substances including water, irrespective of the composition or purity of formaldehyde. As such mixed components, in addition to the mixture of formaldehyde and water, there may be mentioned methyl alcohol, formic acid, methyl formate, methylal or carbon dioxide. A mixture of these substances will not cause detrimental damage nor give advantageous effect on separation between formaldehyde and water. Furthermore, other substances such as higher alcohols, lower content of sugar, polymers of formaldehyde, etc. are also found to be inert to separation.

While the ratio by weight of formaldehyde to water in the feed material is not critical in the present invention, it is usually in the range from 0.25 to 120.0. Furthermore, it has also been found that the process of the present invention is applicable even when the water content in the feed formaldehyde material is 500 ppm or less. Thus, the process of the present invention is effectively applied either in case when the feed material contains equal amounts of formaldehyde and water, thereby to separate into formaldehyde and water, or in case when the feed material consists substantially of formaldehyde with water content of 500 ppm or less, thereby to further purify formaldehyde to water content of 10 ppm or less. According to the experience of the present inventors, purification of formaldehyde up to a grade beyond analysis, perhaps 5 ppm or less, of water content is possible when good apparatus and adsorbents are employed under well controlled conditions.

For the purpose of obtaining a high purity formaldehyde, the process of the present invention is desirably carried out in the following manner. Namely, the separation apparatus is designed in columnar shape and the adsorbents are packed therein as uniformly as possible. A certain volume of the packed adsorbents has an adsorption capacity corresponding to the adsorbents. It has now been found advantageous to consume only a portion of the adsorption capacity of the whole adsorbents packed in a column and then subject said partly consumed adsorbents to regeneration. According to this procedure, a high purity formaldehyde can be recovered, although the whole adsorption capacity of the adsorbents cannot be utilized. Furthermore, desorption of adsorbed water from the column is also carried out advantageously by recovering only a portion of desorbed components, e.g. water, and recycling the remainder of the desorbed components to the column. This is because formaldehyde which may be present in the neighborhood of the adsorbed body may be entrained in the recovered water, if all of the water is recovered by desorption, whereby disposal of recovered water may sometimes be difficult. By such a procedure, there can be obtained high purity streams both of formaldehyde and of water, although recovery per one operation is lowered.

Figure 2:
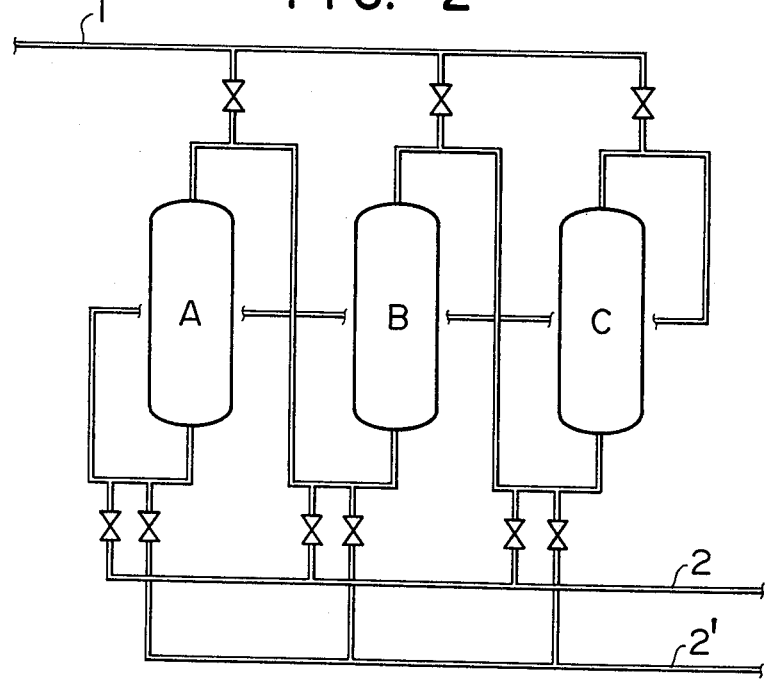

In the accompanying drawings,

FIG. 1 shows schematic flow-sheet of one example of a separation apparatus suitable for practicing the process of the present invention, wherein separation columns A, B and C are connected in parallel with respect to feed line 1 and recovery line 2, 1' shows gas purge line and 2' desorbed gas line; and FIG. 2 shows schematic flow-sheet of another example of separation apparatus for practicing the process of the present invention, wherein separation columns are connected in series via the circulation line 0 and the circulation lines are connected respectively with feed line 1 and recovery lines 2 and 2'.

Referring now to FIG. 1, efficient purification by separation can be effected according to the present process by use of the combination of plural columns connected in parallel as shown in FIG. 1. According to this embodiment, plural columns are connected in parallel to each other and separation operation is conducted continuously while switching the operating column from one to another. In FIG. 1, the columns A, B and C are connected in parallel with respect to feed line 1 and recovery line 2 and can by turns function as adsorption, desorption and preparatory columns, respectively. By use of this apparatus, a high purity formaldehyde can be produced according to the aforesaid preferred embodiment. However, as mentioned above, a high purity formaldehyde can be produced by said embodiment only at the sacrifice of recovery.

FIG. 2 shows another example of the apparatus, by which a high purity formaldehyde can be produced continuously with high recovery. According to one preferred embodiment, an adsorption zone of formaldehyde and water is formed and displaced through plural columns connected in series in a closed recycle system and a stream enriched in formaldehyde is recovered from the forefront portion of the adsorption zone and a stream enriched in water from the rear-end portion of the adsorption zone, respectively, intermittently or continuously. According to further preferred embodiment, while conducting the above procedure, fresh feed of a mixture of formaldehyde and water is charged supplementarily to the central portion of the adsorption zone, intermittently or continuously. When this method is adopted, the formaldehyde and water fed into the column resides in the column and only the separated fractions are recovered. Thus, recovery can be 100% irrespective of the purity of the product.

In FIG. 2, the adsorption zone is now supposed, for example, to be bridging from the lower part of the column A to the upper part of the column C. The adsorption zone is then displaced toward the direction of the column B. When the forefront of the adsorption zone reaches the bottom of the column C or further the column B or bottom of the column A, a portion of separated fraction is removed from each column. Similarly, when the rear-end of the adsorption zone reaches bottom of the column A or further the column C or bottom of the column B, a portion of the separated fraction is removed from each column. Displacement of the adsorption zone may be effected by providing pressure difference between the forefront and rear-end of the adsorption zone or by use of a developing agent. As the displacement proceeds, high purity formaldehyde and water are enriched respectively at both ends of the adsorption zone. When they are removed from the column, there occurs decrease in the material to be separated present in the adsorption zone, whereupon fresh feed material is fed to the central portion of the adsorption zone. Such a procedure is rather complicated and it is also necessary to keep the flow of the gas through the column smooth as a whole.

For conducting operation in a development column, operation conditions should strictly be selected and there have been found preferable adsorbents. Namely, it is recommendable to employ adsorbents shaped in particles with sizes from 4 to 400 mesh, preferably 24 to 100 mesh, or in pellets with sizes from ½ to 1/32 inch, preferably ¼ to ⅛ inch.

The process of the present invention has a variety of applications, most preferably in purification step of formaldehyde monomers for production of polyacetal by polymerization of formaldehyde in commercial industry. According to one typical application, from a starting material comprising 30 to 60% of formaldehyde and 70 to 40% of water there can be obtained formaldehyde with purity of 99.9% or more. In this application, as compared with prior art, the process of the present invention is advantageous in shortage of steps, saving of energy and improvement of the quality of the polymer to be obtained. According to another typical application, formaldehyde separated to water content of 1% or less or over 500 ppm or less can further be subjected to purification by the process of the present invention, whereby a very high purity formaldehyde beyond precision of analysis can be obtained. By use of such a formaldehyde monomer, a high quality polymer can be synthesized.

The present invention is further described in further detail with reference to the following Examples, which are set forth for not limiting but for illustrative purpose only. In the Examples, all "%" are by weight unless otherwise noted.

EXAMPLE 1

A series of experiments were carried out by use of a jacketed cylindrical column of 8 mm in diameter and 200 mm in length. In these experiments, various adsorbents as shown in Table 1 were tested in the following manner. Of these adsorbents, those in Run No. 1 to No. 9 are controls and those in Run No. 10 to No. 16 are within the scope of the invention.

The column packed with adsorbents was maintained at 152° C. Into this column was fed 20 ml of a gaseous mixture comprising 50% of formaldehyde and 50% of water which had been also adjusted at 152° C. under pressure of 780 mm Hg. After 10 seconds after introduction of the mixture, 50 ml of nitrogen gas which had also been adjusted at 152° C. was introduced into the column for purging the column and the gas recovered from the column was subjected to analysis of its composition. Analysis of the gas was conducted by means of high-sensitive gas chromatography equipped with TCD detector. The results are shown also in Table 1. Remarks are given in place of the results of analysis for the experiments in which adsorbents were extremely deteriorated or recovery was very bad.

EXAMPLE 2

Another series of experiments were carried out using the same column as in Example 1 by use of various adsorbents of the present invention as shown in Table 1.

In each experiment, the column packed with the adsorbents was maintained at 148° C. and a gaseous mixture comprising 2% of water and 98% of formaldehyde adjusted at the same temperature was fed thereinto under pressure of 740 mmHg. When 50 ml of the mixture was fed, the effluent gas was recovered and analyzed similarly as in Example 1. The results are shown in Table 2.

EXAMPLE 3

Example 2 was repeated except that the adsorbents which had been subjected to pre-treatment under conditions as shown in Table 3 and formaldehyde containing 450 ppm of water as feed material were used. The results are shown in Table 3.

EXAMPLE 4

A series of experiments were carried out by use of the type A synthetic zeolite containing 94% potassium as exchanged cations shaped in granules or pellets with various sizes as shown in Table 4 which had been pre-treated at 25° C. with 0.01 mol/liter of phosphoric acid. Each experiment was carried out at the temperature and under the pressure as indicated in the Table 4 under otherwise the same conditions as in Example 2. The results are also given in Table 4.

TABLE 1

| Run No. | Adsorbents | Composition (wt. %) | | | | Remarks |
|---|---|---|---|---|---|---|
| | | Formaldehyde | Water | Methyl formate | Others | |
| 1 | Dehydrated cation exchange resins | 57.2 | 40.5 | 2.3 | 0 | |
| 2 | Porous styrene-divinyl benzene copolymer | 50.1 | 48.4 | 1.5 | 0 | |
| 3 | Silica gel | 60.2 | 17.6 | 22.2 | small amount | Reactivation impossible, adsorbed amount reduced in the second time |
| 4 | Carbon beads | — | — | — | large amount | Formation of sugar, poor recovery |
| 5 | Type X zeolite (commercially available, | — | — | — | — | Polymers, decomposed substances and |

TABLE 1-continued

| Run No. | Adsorbents | Composition (wt. %) | | | | Remarks |
|---|---|---|---|---|---|---|
| | | Formaldehyde | Water | Methyl formate | Others | |
| | sodium form) | | | | | sugar formed (carbonized) |
| 6 | Type X zeolite (commercially available, potassium form) | — | — | — | — | Polymers, decomposed substances and sugar formed (carbonized) |
| 7 | Type Y zeolite (commercially available, sodium form) | — | — | — | — | Polymers, decomposed substances and sugar formed (carbonized) |
| 8 | Type 5A zeolite (commercially available, calcium form) | — | — | — | — | Decomposed substances and sugar formed |
| 9 | Type 4A zeolite (commercially available, sodium form) | — | — | — | large amount | Sugar and decomposed substances formed |
| 10 | Type A zeolite (94% potassium form) | 95.9 | 0.1 | 4.0 | 0 | |
| 11 | Type A zeolite (85% barium form) | 98.2 | 0.5 | 1.3 | small amount | |
| 12 | Type A zeolite (53% potassium and 41% cesium form) | 96.3 | 0.2 | 3.5 | small amount | |
| 13 | Type A zeolite (29% potassium and 66% rubidium form) | 95.1 | 0.3 | 4.6 | small amount | |
| 14 | Type A zeolite (58% barium and 38% potassium form) | 98.5 | 0.1 | 1.4 | small amount | |
| 15 | Type A zeolite (67% barium and 25% cesium form) | 98.0 | 0.3 | 1.7 | small amount | |
| 16 | Type A zeolite (45% barium and 46% rubidium form) | 97.8 | 0.8 | 1.4 | small amount | |

Note:
Zeolites in Run No. 10-16 were prepared by contacting sodium form Type A zeolites with 0.5 mole/liter of aqueous solutions of chlorides of the corresponding exchanged cations, respectively, in a jacketed cylindrical column at 90° C. for 48 hours.

TABLE 2

| Run No. | Type A zeolite | | Impurities (ppm) | |
|---|---|---|---|---|
| | First cation (%) | Second cation (%) | Water | Methyl formate |
| 101 | Potassium (95.2) | — | 380 | 8900 |
| 102 | Barium (95.1) | — | 950 | 12400 |
| 103 | Cesium (33.6) | — | 1800 | 15000 |
| 104 | Rubidium (65.3) | — | 1240 | 18900 |
| 105 | Potassium (77.8) | Barium (18.2) | 490 | 11200 |
| 106 | Potassium (88.4) | Cesium (6.7) | 380 | 13300 |
| 107 | Potassium (89.8) | Rubidium (6.2) | 720 | 14800 |
| 108 | Barium (91.3) | Cesium (4.7) | 1110 | 18100 |
| 109 | Barium (85.3) | Rubidium (10.7) | 1590 | 14000 |
| 110 | Potassium (99.3) | — | 120 | 12400 |
| 111 | Potassium (89.0) | — | 450 | 58000 |

TABLE 3

| Run No. | Type A zeolite | | | Impurities of product (ppm) | |
|---|---|---|---|---|---|
| | Replaced cation | Treating agent | Treatment conditions | Water | Methyl formate |
| 201 | Potassium (94%) | Phosphoric acid | 0.05 mole/liter, 25° C., 20 minutes | <40 | 1130 |
| 202 | Potassium (94%) | Potassium dihydrogen phosphate | 0.05 mole/liter, 25° C., 20 minutes | " | 1035 |
| 203 | Potassium (94%) | Potassium hydrogen phosphate | 0.05 mole/liter, 25° C., 20 minutes | " | 1080 |

TABLE 3-continued

| Run No. | Type A zeolite Replaced cation | Treating agent | Treatment conditions | Impurities of product (ppm) Water | Methyl formate |
|---|---|---|---|---|---|
| 204 | Potassium (94%) | Potassium phosphate | 0.05 mole/liter, 25° C., 20 minutes | " | 1121 |
| 205 | Potassium (94%) | Ammonia | 760 mm/Hg, 20° C., 2 hours | " | 1180 |
| 206 | Potassium (94%) | Tri-methylamine | 2% aqueous solution, 25° C., 2 hours | " | 1220 |
| 207 | Potassium (94%) | Pyridine | 2% aqueous solution, 25° C., 2 hours | " | 1540 |
| 208 | Potassium (94%) | Formaldehyde | 700 mm/Hg, 170° C., 16 hours | " | 1120 |
| 209 | Potassium (via hydrogen form) | — | — | " | about 10000 |
| 210 | Potassium (via hydrogen form) | Phosphoric acid | 0.02 mole/liter, 25° C., 20 minutes | " | 520 |
| 211 | Potassium (via hydrogen form) | Potassium phosphate | 0.02 mole/liter, 25° C., 20 minutes | " | 1330 |
| 212 | Potassium (via hydrogen form) | Ammonia | 200 mm/Hg, 100° C., 2 hours | " | 1750 |
| 213 | Potassium (via hydrogen form) | Formaldehyde | 600 mm/Hg, 180° C., 16 hours | " | 1180 |
| 214 | Barium | Phosphoric acid | 0.08 mole/liter, 25° C., 20 minutes | " | 510 |
| 215 | Barium (via hydrogen form) | Phosphoric acid | 0.08 mole/liter, 25° C., 20 minutes | " | 1220 |

Note:
The zeolites Run No. from 209 to 213 and 215 are prepared by treating first sodium form type A zeolites with ammonia gas, heating the product in steam and then converting hydrogen to corresponding cations as described in Table 1.

TABLE 4

| Run No. | Adsorbents Shape | Size | Impurities in product (ppm) Water | Methyl Formate |
|---|---|---|---|---|
| 301 | granule | 4 mesh | 80 | 1220 |
| 302 | " | 48 mesh | <40 | 980 |
| 303 | " | 150 mesh | " | 950 |
| 304 | pellet | 1 inch | 180 | 1300 |
| 305 | " | ⅛ inch | <40 | 1180 |
| 306 | " | 1/32 inch | " | 1540 |

EXAMPLE 5

The same starting material as used in Example 1 was fed to the same appratus as in Example 1 under the same conditions as in Example 1 and feeding was discontinued after 60% as much as the adsorption capacity of the starting material had been fed. Subsequently, preceding fractions corresponding to 70% of the total eluate desorbed with nitrogen gas were recycled to the column and succeeding fractions corresponding to 30% of the total eluate were recovered. The first fraction of the effluent gas was found to be formaldehyde with water content of 40 ppm or less. The eluate gas recovered was found to be water containing 1.2% of formaldehyde.

EXAMPLE 6

Three stainless columns, each being 8 cm in diameter and 50 cm in length with effective inner volume of 200 ml, were prepared and arranged in the same manner as shown in FIG. 1. In each column was packed the same zeolite as used in Run No. 210 in Example 3. From the top of the column A was fed the feed gas having the same composition as used in Example 3 through the line 1 at 140° C. under pressure of 740 mmHg thereby to carry out separation. The water content in the formaldehyde recovered from the line 2 was found to be 40 ppm or less. After feeding was continued for 2 hours at the rate of 50 ml/hour, the separation line was switched from column A to column B and nitrogen gas maintained at 148° C. under pressure of 740 mmHg was fed to column A at the rate of 250 ml/hour, followed by feeding of nitrogen gas maintained at 165° C. under pressure of 740 mmHg for one hour and further by feeding of nitrogen gas maintained at 148° C. under pressure 740 mmHg for one hour. During these procedures, separation operation was continued in column B and column C successively. In each column, after separation operation, desorption operation with nitrogen gas was conducted in the same manner as in column A. Thus, formaldehyde dehydrated to 40 ppm or less was obtained continuously at the rate of 50 ml/hour.

What we claim is:

1. A process for purification of formaldehyde by separation, which comprises contacting with adsorbents selected from the group consisting of type A synthetic zeolites wherein the exchangeable cations contain at least one of the Group IA, from the fourth to the sixth period, and Group IIA, the sixth period, of the Periodic Table of Elements a solution containing water, formaldehyde and a stabilizer against polymerization of formaldehyde thereby selectively to adsorb water on said adsorber and to leave a stream enriched in formaldehyde and containing the stabilizer.

2. A process as in claim 1, wherein the exchangeable cations in the type A synthetic zeolite are composed of 90 wt.% or more of potassium ions or barium ions.

3. A process as in claim 1, wherein the exchangeable cations in the type A synthetic zeolite are composed of 90 wt.% or more of barium, or barium and potassium.

4. A process as in claim 1, wherein the type A synthetic zeolite is subjected to pre-treatment with treating agents selected from the group consisting of formaldehyde, ammonia, amines, urea compounds and phosphoric acid compounds.

5. A process as in claim 4, wherein the treating agent is phosphoric acid.

6. A process as in claim 1, wherein the type A synthetic zeolite is produced by replacing the type A synthetic zeolite in hydrogen form with cations of the Group IA, from the fourth to the sixth period, or Group IIA, the sixth period, of the Periodic Table of Elements.

7. A process as in claim 6, wherein the type A synthetic zeolite is subjected to pre-treatment with treating agents selected from the group consisting of formaldehyde, ammonia, amines, urea compounds and phosphoric acid compounds.

8. A process as in claim 7, wherein the treating agent is phosphoric acid.

9. A process as in claim 1, wherein the stabilizer is selected from the group consisting of methyl alcohol, formic acid, methyl formate, methylal and carbon dioxide.

10. A process as in claim 1, wherein the ratio by weight of formaldehyde to water is in the range from 0.25 to 120.0.

11. A process as in claim 1, wherein the mixture of formaldehyde and water is formaldehyde with water content of 500 ppm or less.

12. A process as in claim 1, wherein the adsorbents are packed in a development column and the adsorbents on consumption of a part of adsorption capacity are subjected to regeneration.

13. A process as in claim 12, wherein a part of the components eluted from the adsorbents is recovered and the remainder thereof is recycled to the column.

14. A process as in claim 13, wherein the adsorbents are shaped in particles with sizes from 20 to 400 mesh or in pellets with sizes from ½ to 1/32 inch.

15. A process as in claim 1, wherein the adsorbents are packed in plural columns provided in parallel to each other, and separation is operated continuously by switching from one column to another, successively.

16. A process as in claim 1, wherein separation is operated by use of plural columns packed with the adsorbents and connected in series in a closed recycle system, by forming an adsorption zone of formaldehyde and water and displacing said zone through said plural columns, and recovering a stream enriched in formaldehyde from the forefront portion of said adsorption zone and a stream enriched in water from the rear-end portion of said adsorption zone, respectively.

17. A process as in claim 16, wherein fresh feed of a mixture containing formaldehyde and water is charged supplementarily to the central portion of the adsorption zone.

* * * * *